United States Patent [19]
Guillemet et al.

[11] Patent Number: 6,022,754
[45] Date of Patent: Feb. 8, 2000

[54] ELECTRONIC DEVICE AND METHOD FOR FORMING A MEMBRANE FOR AN ELECTRONIC DEVICE

[75] Inventors: Jean-Paul Guillemet, Toulouse; Myriam Combes, Paisance Du Touch; Stephane Astie, Radel; Emmanuel Scheid, Corronsac, all of France

[73] Assignee: Motorola, Inc., Schaumburg, Ill.

[21] Appl. No.: 09/120,755

[22] Filed: Jul. 22, 1998

[51] Int. Cl.⁷ .................................................. G01N 27/12
[52] U.S. Cl. ................................................ 438/49; 438/48
[58] Field of Search ........................................ 438/49, 48

[56] References Cited

U.S. PATENT DOCUMENTS 4,706,493  11/1987  Chang et al. .
5,545,300  8/1996  Yun et al. .

OTHER PUBLICATIONS

Stanley Wolf and richard N. Tauber, Silicon Processing for the VLSI Era, 1986.

*Primary Examiner*—Charles Bowers
*Assistant Examiner*—Martin Sulsky
*Attorney, Agent, or Firm*—Rennie W. Dover

[57] ABSTRACT

An electronic device comprises a semiconductor substrate (2) having a cavity (32) extending into the substrate (2), a membrane (8) formed over the semiconductor substrate so as to extend across the cavity (32) in the semiconductor substrate and an active region (14, 30) supported by the membrane (8) and positioned adjacent the cavity (32). The membrane (8) comprises a single dielectric layer formed of an oxy-nitride material.

21 Claims, 3 Drawing Sheets

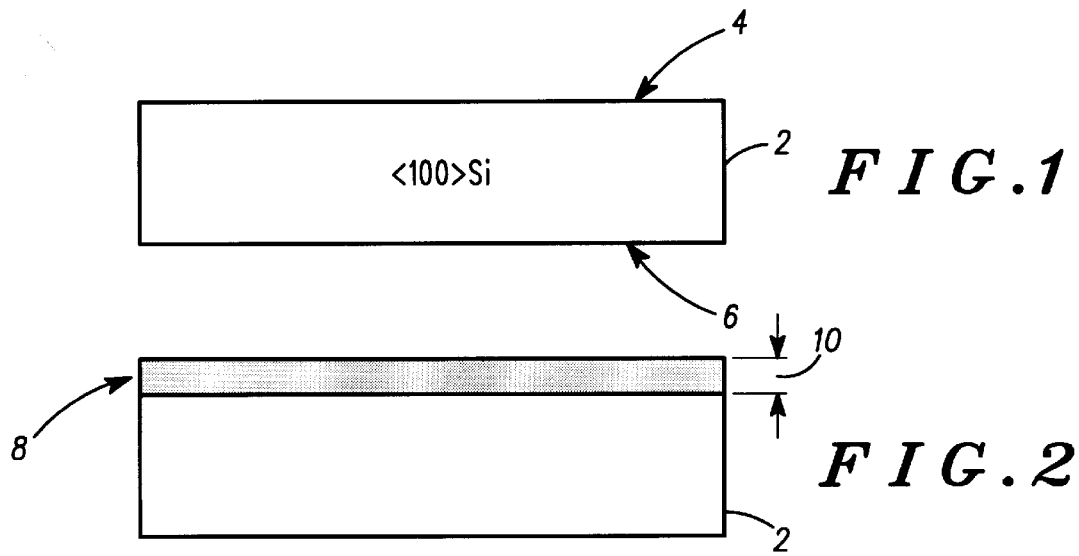

6,022,754

1

ELECTRONIC DEVICE AND METHOD FOR FORMING A MEMBRANE FOR AN ELECTRONIC DEVICE

FIELD OF THE INVENTION

This invention relates in general to electronic devices and a method for forming electronic devices. More particularly, this invention relates to low power electronic devices and a method for their manufacture.

BACKGROUND OF THE INVENTION

A chemical sensor is a device which monitors the concentration of a given chemical species in a liquid or a gas. Chemical sensor devices comprise a sensitive layer, which is sensitive to a particular chemical which is to be detected by the sensor device, and a heater integrated on a semiconductor substrate such as a silicon substrate. The heater increases the temperature of the sensitive layer to increase the sensitivity of the sensor device and is typically required to heat the sensitive layer to temperatures in the range of 25° C. to 600° C. during operation of the sensor device. At these temperatures, there is significant loss of thermal energy through the silicon substrate and therefore such devices suffer from high power consumption.

The high power consumption is a particular problem when the sensor device is required to be powered by a battery. For example, some applications may require battery back-up operation. For such battery powered applications, the power consumption should be around 60 mw at 400° C. in DC mode.

In order to reduce the power consumption in semiconductor chemical sensors, it has been proposed, see for example French Patent Application no. FR-A-2615287, to micromachine the backside of the bulk silicon substrate to form a thin membrane under the active region of the sensor device (i.e. under the heater and sensitive layer). The thin membrane is formed by depositing a solution of Boron Oxide ($B_2O_3$) by spin-on onto the silicon substrate and by then diffusing the boron dopant into the substrate. Although this technique reduces the thermal losses to the bulk silicon substrate, since the membrane comprises a silicon layer doped with P+ type material, which material has a high thermal conductivity (35 $Wm^{-1}K^{-1}$), the thermal losses during use of the sensor and hence power consumption is still too high for low power operation, such as battery back-up operation. For example, at 400° C., the power consumption for such a sensor can be as high as 200 mW in DC mode.

Another technique for reducing thermal loss is described in U.S. Pat. No. 5,545,300. This patent describes using a composite membrane comprising a glass film formed over a silicon nitride film. The reduction in the power consumption with the described technique is limited due to the high thermal conductivity of the silicon nitride film (23 $Wm^{-1}K^{-1}$) used in the composite membrane. The power consumption of the device disclosed in this patent is close to 110 mW at 400° C. in DC mode, which is still too high for battery operation.

Since two different steps (deposition of silicon nitride film followed by deposition of silicon oxide film) are required to realise the membrane, this patent also suffers from the cost disadvantage mentioned above of having several fabrication steps. A further disadvantage of the process described in this patent is that as the silicon nitride layer is deposited on top of the silicon substrate, such a process step can create dislocations on the silicon surface which is not compatible

2 with integrated circuit (IC) technology. In other words, with such a process, it would not be possible to integrate the control chip on the same substrate as the sensor device.

An article entitled 'Reduction of heat loss of silicon membranes by the use of trench-etching techniques' by J. Werno, R. Kersjes, W. Mokwa and H. Vogt, and published on pages 578–581 of Sensors and Actuators A, 41–42 (1994), describes a solution to improve the thermal insulation of single crystal silicon membranes by means of oxide-filled trenches. The power consumption of this solution is 230 mW at 400° C. in DC mode, which is too high for battery operation. In addition, the described trench-etching technique employs three successive process steps (SIMOX/epitaxy/oxide-filled trenches) and is thus an expensive technique to use with respect to the manufacturing costs.

There is therefore a need to provide an improved electronic device which can be operated at low power and a method of forming such an electronic device.

SUMMARY OF THE INVENTION

In accordance with an aspect of the present invention there is provided a method of forming a membrane for supporting an active region of an electronic device. In accordance with an embodiment of the present invention, a semiconductor substrate is provided and a membrane is formed over the semiconductor substrate, wherein the membrane comprises a single dielectric layer of an oxy-nitride material. An active region of the electronic device is formed over the single dielectric layer. A portion of the semiconductor substrate is removed so as to provide a cavity in the substrate, wherein the single dielectric layer extends across the cavity.

BRIEF DESCRIPTION OF THE DRAWINGS

An electronic device and a method for forming an electronic device in accordance with the present invention will now be described, by way of example only, with reference to the accompanying drawings in which:

FIGS. 1–9 show simplified schematic cross-sectional diagrams of a portion of an electronic device in accordance with the present invention during various stages of fabrication.

DETAILED DESCRIPTION OF THE DRAWINGS

Figure 6:
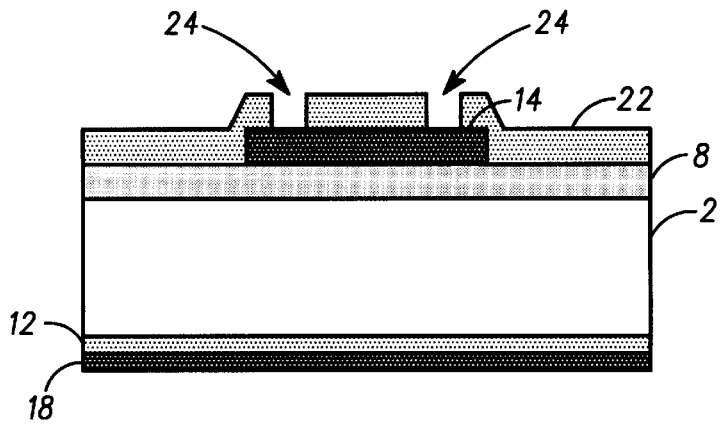

In the following description, the invention will be described in relation to a chemical sensor device. It will however be appreciated that the present invention may apply to any other electronic devices, such as thermal sensors, calorimetric sensors, pressure sensors, microphones, inkjet sensors, micropumps, and Microsystems, which use a membrane to support the active region of the electronic device over a cavity in the bulk substrate.

A method for forming a chemical sensor device in accordance with a preferred embodiment of the present invention will now be described with reference to FIGS. 1–9 of the drawings which are simplified schematic cross-sectional diagrams of a portion of the chemical sensor device during various stages of fabrication. Although in the following description the semiconductor substrate, layers and regions will be described as having certain conductivity types and being comprised of certain material, this is for illustrative purposes only. It is not intended that the invention be limited to the specific conductivity types nor the specific materials referred to herein.

Referring firstly to FIG. 1, a semiconductor substrate 2, preferably a silicon <100> substrate, is provided. The semiconductor substrate 2 has a first surface 4 and a second surface 6, which is opposite the first surface 4. A dielectric layer 8 of an oxy-nitride material is formed over semiconductor substrate 2 on the first surface 4, see FIG. 2. The dielectric layer 8 has a thickness 10 in the range 30 nanometres to 3 micrometers.

In the preferred embodiment, the dielectric layer 8 is formed of a silicon oxy-nitride material having a composition $SiO_xN_y$. The composition (i.e. the values of x and y) is selected so that the dielectric layer 8 has good mechanical properties and low thermal conductivity in the range 1–30 $Wm^{-1}K^{-1}$ (preferably 5 $Wm^{-1}K^{-1}$). A dielectric layer 8 having good mechanical properties ensures high manufacturing yield of the device (up to 100%).

The mechanical properties of the dielectric layer 8 depend upon the Young's Modulus of the silicon oxy-nitride material, which forms the dielectric layer 8, and the thermal expansion of the silicon oxy-nitride material. The composition of the silicon oxy-nitride material is selected so that the thermal expansion of the material is substantially equal to that of the substrate material. In the preferred embodiment which has a silicon substrate, the composition is chosen so that the thermal expansion of the silicon oxy-nitride material is substantially equal to the thermal expansion of silicon (that is, $2.5 \times 10^{-6}/°$ C.). This ensures that the dielectric layer 8 has a low residual stress level.

The composition of the silicon oxy-nitride material is also selected so that the Young's Modulus is close to that of the substrate material. Since silicon has a Young's Modulus of 170 GPa, the silicon oxy-nitride material is arranged to have a Young's Modulus in the range 100–180 GPa.

The dielectric layer 8 can be formed by Plasma Enhanced Chemical Vapour Deposition (PECVD) or Chemical Vapour Deposition (CVD). PECVD is preferred because it is easier to control the composition of the oxy-nitride material by adjusting the pressure and power of the plasma and hence the oxy-nitride dielectric layer 8 can be optimised both for low thermal conductivity and for low stress.

In the preferred embodiment, a mixture of silane, ammonia, nitrous oxide and nitrogen in a 0.17:0.14:0.14:0.55 ratio respectively is used in a PECVD process to provide a dielectric layer 8 having a composition $SiO_xN_y$, where x=0.89, and y=0.74. The PECVD process is carried out in a CVD 5000 chamber supplied by Applied Materials Inc., which chamber is heated to a temperature of 400° C. The plasma pressure is 4.5 Torr and the plasma power is 325 W.

Referring now also to FIG. 3, a silicon oxide layer 12 is formed on the second surface 6 of the semiconductor substrate 2. The silicon oxide layer 12 can be formed by thermal oxidation of the silicon substrate or by PECVD or by CVD. Thermal oxidation is preferred because during the oxidation of the silicon substrate, the dielectric layer 8 is annealed at the same time.

A conductive layer is formed over the dielectric layer 8. The conductive layer is then patterned and etched to leave a portion 14 of the conductive layer which forms a heater 14 of the chemical sensor device, see FIG. 4. The conductive layer comprises a polysilicon layer or a metal layer having good conductivity: the resistivity is in the range $10^{-6}$ ohm.cm to $10^{-3}$ ohm.cm. The thickness 16 of the conductive layer 14 is between 30 nanometres and 3 micrometres.

In FIG. 5, a masking layer 18 is formed over the silicon oxide layer 12 on the backside of the semiconductor substrate 2. The thickness 20 of the masking layer 18 is between 30 nanometres and 3 micrometres. In the preferred embodiment, a silicon nitride masking layer is PECVD deposited on the silicon oxide layer 12 using the same equipment used for PECVD deposition of the dielectric layer 8. The silicon oxide layer 12 is required since the silicon nitride masking layer 18 has poor adherence to the silicon substrate 2. The masking layer 18 is used as a backside hard mask during backside micromachining of the bulk silicon substrate 2. Alternatively, a silicon oxy-nitride layer could be used as the masking layer 18 due to the very low etch rate of silicon oxy-nitride in potassium hydroxide solution, which solution is used to etch the semiconductor substrate 2.

A first insulating layer 22 is then deposited over the dielectric layer 8 and the portion 14 of the conductive layer. In the preferred embodiment, the first insulating layer 22 comprises a silicon dioxide layer, which is deposited on the dielectric layer 8 by PECVD or a Low Pressure Chemical Vapour Deposition LPCVD. The first insulating layer 22 is patterned and etched to form contact openings 24 extending to the conductive layer (FIG. 6).

Figure 7:
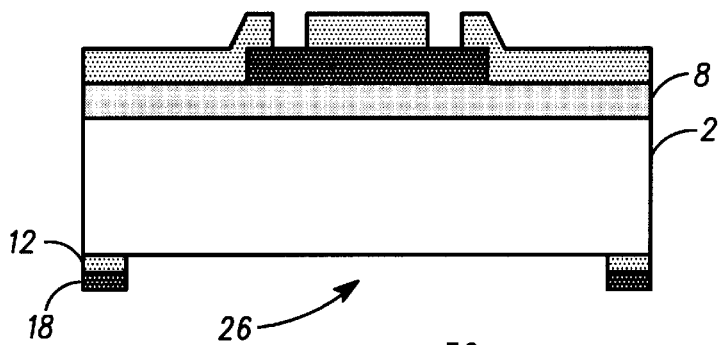

In FIG. 7, the masking layer 18 is patterned and then the masking layer 18 and the silicon oxide layer 12 are etched to form an opening 26 extending to the second surface 6 of the semiconductor substrate 2. The opening 26 defines the area for etching the semiconductor substrate 2.

Figure 8:
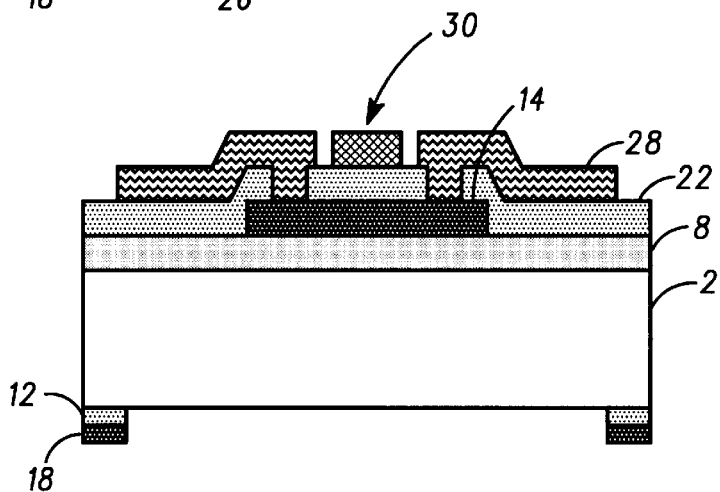

A sensitive layer 30 is then formed on a portion of the first insulating layer 22 so that it overlies the heater 14 (FIG. 8). The sensitive layer 30 is formed by first depositing (by sputtering, evaporating, CVD or spin-on) a layer of material which is sensitive to the chemical species to be sensed by the sensor device over the whole of the device and then using patterning to remove portions of the layer to leave the sensitive layer 30. In the preferred embodiment, the sensitive material is a metal oxide and a standard lift-off technique is used. Polymeric sensing materials may also be used.

Electrical contact is then made to the heater 14 and the sensitive layer 30. Metallisation, such as chromium/titanium/platinum metallisation, is formed over the wafer by evaporation. The metallisation is then patterned by lift-off or etching to leave heater metal conductors 28 (FIG. 8) and sensitive layer metal conductors (not shown).

Figure 9:
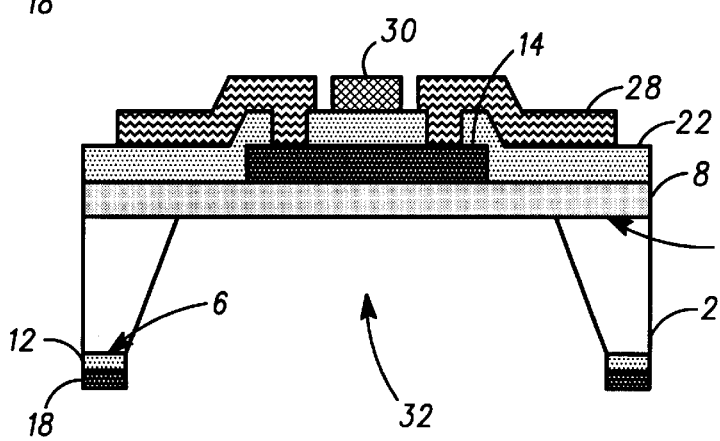

In order to improve thermal isolation of the active region of the chemical sensor device, which region includes the sensitive layer 30 and the heater 14, the semiconductor substrate 2 is etched or bulk-micromachined through the opening 26 to form a cavity 32 which extends from the second surface 6 to the first surface 4 of the semiconductor substrate 2 as shown in FIG. 9. The single dielectric layer 8 of oxy-nitride material forms the membrane of the chemical sensor device in accordance with the present invention, which membrane extends at least across the cavity 32 and supports the active region of the chemical sensor device.

The bulk-micromachining process is an anisotropic etch process. In the preferred embodiment, a wet etch solution comprising potassium hydroxide (KOH) is used to remove the bulk of the silicon substrate 2. Since oxy-nitride material has a very low etch rate in KOH (0.04 micrometres per hour), the dielectric layer 8 acts as an etch stop layer. Table 1 below gives data on the KOH mechanical yield and etch rate at 90° C. for different kinds of membranes.

TABLE 1

| Membrane Material | KOH Yield (%) | KOH Etch Rate (μm/h) |
|---|---|---|
| Oxide | 20 | 0.25 |
| Oxy-Nitride | 100 | 0.04 |
| Nitride/Oxide | 95 | 0.02 |
| Trenches | N/A | 0.25 |
| P+ Silicon | 100 | 15 |

This very low etch rate means that the thickness of the dielectric membrane 8 can be accurately controlled, and hence the same power consumption of the sensor device can be controlled, over a wafer, wafer to wafer and lot to lot. As can be seen from the etch rates given in Table 1, this is not the case with a P+ silicon layer which forms the membrane in the above described French Patent Application No. FR-A-2615287.

Table 1 also shows the mechanical yield for membranes of different types of material. An oxy-nitride membrane deposited by PECVD in accordance with the present invention, as can be seen from Table 1, has good mechanical properties.

In the preferred embodiment described above, a portion of the silicon substrate is removed by backside micromachining using a wet etch process. Other techniques for removing the silicon substrate so as to leave a membrane over a cavity may also be used. For example, the silicon substrate may be surface micromachined using a wet etch process (on first surface 4), or the silicon substrate may be backside or surface micromachined using a dry etch process, such as plasma etching, or a direct wafer bonding technique may be used. For the latter technique, two wafers are bonded together and then one wafer is micromachined to provide the membrane.

The oxy-nitride membrane 8 of the present invention provides low heat conduction after bulk substrate removal and also acts as an insulating layer between the heater and the substrate. The effectiveness of the thermal isolation provided by the membrane is determined by the thermal conductivity of the PECVD oxy-nitride membrane, which mainly depends on the composition of the membrane.

Figure 10:
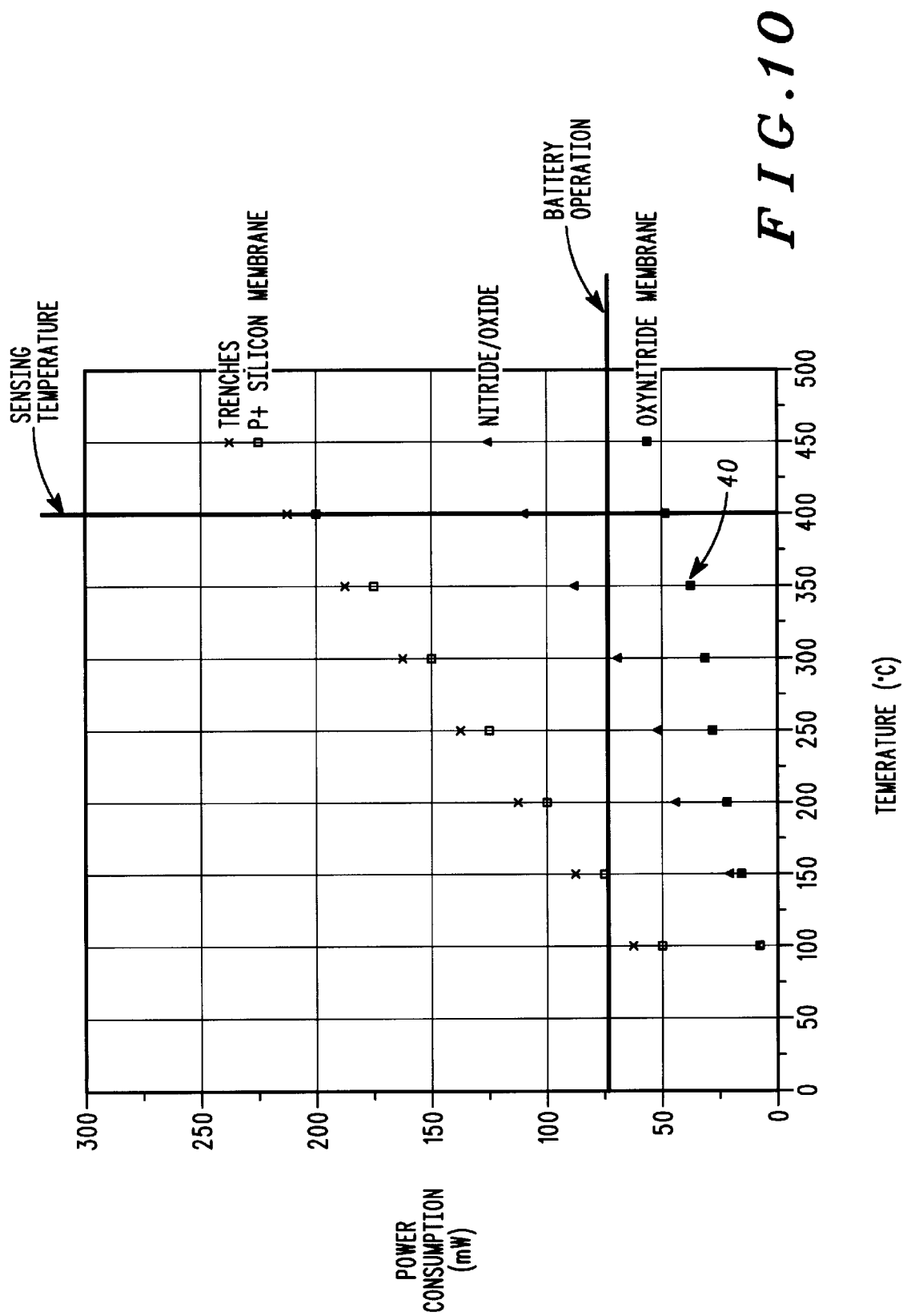
FIG. 10 shows a graph of power consumption as a function of temperature for different types of membranes.

FIG. 10 shows a graph of the power consumption as a function of temperature for different types of membrane. As shown by curve 40, the oxy-nitride membrane in accordance with the present invention meets the low power requirements for battery operation across a wide temperature range.

In summary, the present invention provides a device having a membrane to support the active region of the device comprising a single dielectric layer of oxy-nitride material having low thermal conductivity (i.e. low power consumption), low stress level, very low etch rate in KOH and which only requires a single process step. The invention therefore provides a membrane which can support low power operation, such as battery back-up, and which is simple and not expensive to manufacture.

We claim:

1. A method for forming a membrane for supporting an active region of an electronic device, the method comprising the steps of:

providing a semiconductor substrate formed of a semiconductor material;

forming a membrane over the semiconductor substrate comprising a single dielectric layer of an oxy-nitride material, the composition of the oxy-nitride material being selected such that the oxy-nitride material has a Young's Modulus substantially the same as the Young's Modulus of the substrate semiconductor material, a thermal expansion substantially the same as the substrate semiconductor material and a thermal conductivity in the range 1–30 $Wm^{-1}K^{-1}$;

forming the active region of the electronic device over the single dielectric layer; and removing a portion of the semiconductor substrate so as to provide a cavity in the substrate, the single dielectric layer extending across the cavity.

2. A method according to claim 1 wherein the semiconductor substrate has a first surface and a second surface, wherein the step of forming the membrane comprises forming the membrane over the first surface of the semiconductor substrate and wherein the step of removing a portion of the semiconductor substrate comprises the steps of:

forming a masking layer over the second surface of the semiconductor substrate after forming the membrane;

removing a portion of the masking layer so as to provide an opening extending through the masking layer to the second surface; and etching the semiconductor substrate through the opening so as to provide the cavity extending between the second surface and the membrane.

3. A method according to claim 2 wherein the etching step comprises wet etching the semiconductor substrate with a solution comprising potassium hydroxide.

4. A method according to claim 1 wherein the forming a membrane step comprises depositing a single dielectric layer of an oxy-nitride material on the semiconductor substrate.

5. A method according to claim 1 wherein the semiconductor substrate is formed of a semiconductor material and the oxy-nitride material is a silicon oxy-nitride material having a composition $SiO_xN_y$, wherein x, and y are selected such that the silicon oxy-nitride material has a Young's Modulus substantially the same as the Young's Modulus of the substrate semiconductor material, a thermal expansion substantially the same as the substrate semiconductor material and a thermal conductivity in the range 1–30 $Wm^{-1}K^{-1}$.

6. A method according to claim 1 wherein the oxy-nitride material has a composition $SiO_xN_y$, where x=0.89, and y=0.74.

7. A method for forming a semiconductor sensor device, the method comprising the steps of:

providing a substrate of a semiconductor material and having a first and a second surface opposite the first surface;

forming a single dielectric layer of an oxy-nitride material over the first surface of the substrate, the composition of the oxy-nitride material being selected such that the oxy-nitride material has a Young's Modulus substantially the same as the Young's Modulus of the substrate, a thermal expansion substantially the same as the substrate and a thermal conductivity in the range 1–30 $Wm^{-1}K^{-1}$;

forming a conductive layer on a portion of the single dielectric layer;

forming a masking layer on the second surface of the substrate;

forming a first insulating layer over the single dielectric layer and the conductive layer;

removing portions of the first insulating layer to form contact openings extending to the conductive layer;

removing a portion of the masking layer to provide an opening extending to the second surface of the substrate;

forming a sensitive layer over a portion of the first insulating layer such that the sensitive layer extends over the conductive layer;

forming electrical contacts to the conductive layer and the sensitive layer; and removing a portion of the substrate through the opening so as to provide a cavity in the substrate extending between the second surface and the single dielectric layer, wherein the single dielectric layer forms a membrane of the sensor device extending at least across the cavity.

8. A method according to claim 7 wherein the oxy-nitride material is a silicon oxy-nitride material having a composition $SiO_xN_y$, wherein x, and y are selected such that the silicon oxy-nitride material has a Young's Modulus substantially the same as the Young's Modulus of the substrate semiconductor material, a thermal expansion substantially the same as the substrate semiconductor material and a thermal conductivity in the range 1–30 $Wm^{-1}K^{-1}$.

9. A method according to claim 7 wherein the oxy-nitride material has a composition $SiO_xN_y$, where x=0.89, and y=0.74.

10. A method according to claim 7, wherein the step or removing a portion of the substrate through the opening includes wet etching the semiconductor substrate with a solution comprising potassium hydroxide.

11. A method according to claim 8, wherein the oxy-nitride material has a composition $SiO_xN_y$ where x=0.89 and y=0.74.

12. A method according to claim 7, wherein the step of forming a single dielectric layer of an oxy-nitride material over the first surface of the substrate comprises depositing the single dielectric layer of oxy-nitride material on the semiconductor substrate.

13. A method for forming a membrane for supporting an active region of an electronic device, the method comprising the steps of:

providing a semiconductor substrate having a cavity extending into the substrate;

forming a membrane over the semiconductor substrate, the membrane comprising a single dielectric layer of an oxy-nitride material, the composition of the oxy-nitride material being selected such that the oxy-nitride material has a Young's modulus substantially the same as the Young's Modulus of the semiconductor substrate, a thermal expansion substantially the same as the semiconductor substrate and a thermal conductivity in the range 1–30 $Wm^{-1}K^{-1}$; and forming the active region of the electronic device over the single dielectric layer.

14. A method for forming a membrane for supporting an active region of an electronic device, the method comprising the steps of:

providing a semiconductor substrate, wherein the semiconductor substrate comprises a silicon substrate and the masking layer comprises a silicon oxide layer over the second surface and a silicon nitride layer over the silicon oxide layer;

forming a membrane comprising a single dielectric layer of an oxy-nitride material over the first surface of the semiconductor substrate, the composition of the oxy-nitride material being selected such that the oxy-nitride material has a Young's Modulus substantially the same as the Young's Modulus of the semiconductor substrate, a thermal expansion substantially the same as the semiconductor substrate and a thermal conductivity in the range 1–30 $Wm^{-1}K^{-1}$, forming the active region of the electronic device over the single dielectric layer; and removing a portion of the semiconductor substrate so as to provide a cavity in the substrate, the single dielectric layer extending across the cavity, wherein the step of removing the portion of the semiconductor substrate further comprises the steps of:

forming a masking layer over the second surface of the semiconductor substrate after forming the membrane;

removing a portion of the masking layer so as to provide an opening extending through the masking layer to the second surface; and etching the semiconductor substrate through the opening so as to provide the cavity extending between the second surface and the membrane.

15. A method according to claim 14 wherein the forming a membrane step comprises depositing a single dielectric layer of an oxy-nitride material on the semiconductor substrate.

16. A method according to claim 14, wherein the oxy-nitride material has a composition $SiO_xN_y$ where x=0.89 and y=0.74.

17. A method according to claim 15 wherein the semiconductor substrate is formed or a semiconductor material and the oxy-nitride material is a silicon oxy-nitride material having a composition $SiO_xN_y$, wherein x, and y are selected such that the silicon oxy-nitride material has a Young's Modulus substantially the same as the Young's Modulus of the substrate semiconductor material, a thermal expansion substantially the same as the substrate semiconductor material and a thermal conductivity in the range 1–30 $Wm^{-1}K^{-1}$.

18. A method according to claim 17, wherein the oxy-nitride material has a composition $SiO_xN_y$ where x=0.89 and y=0.74.

19. A method according to claim 14 wherein the semiconductor substrate is formed of a semiconductor material and the oxy-nitride material is a silicon oxy-nitride material having a composition $SiO_xN_y$, wherein x and y are selected such that the silicon oxy-nitride material has a Young's Modulus substantially the same as the Young's Modulus of the substrate semiconductor material, a thermal expansion substantially the same as the substrate semiconductor material and a thermal conductivity in the range 1–30 $Wm^{-1}K^{-1}$.

20. A method according to claim 14, wherein the oxy-nitride material has a composition $SiO_xN_y$ where x=0.89 and y=0.74.

21. A method according to claim 14, wherein the oxy-nitride material has a composition $SiO_xN_y$ where x=0.89 and y=0.74.

* * * * *

UNITED STATES PATENT AND TRADEMARK OFFICE
CERTIFICATE OF CORRECTION

PATENT NO.     : 6,022,754
DATED          : February 8, 2000
INVENTOR(S)    : Jean-Paul Guillemet et al.

Page 1 of 1

It is certified that error appears in the above-identified patent and that said Letters Patent is hereby corrected as shown below:

<u>Column 7,</u>
Line 27, delete "or" and add -- of --.

<u>Column 8,</u>
Line 35, delete "or" and add -- of --.

Signed and Sealed this

Twenty-first Day of May, 2002

Attest:

Attesting Officer

JAMES E. ROGAN
*Director of the United States Patent and Trademark Office*